(12) United States Patent
Regev

(10) Patent No.: US 10,856,746 B2
(45) Date of Patent: Dec. 8, 2020

(54) SYSTEM AND METHOD FOR ESTIMATING VITAL SIGNS

(71) Applicant: Essence Smartcare Ltd., Herzlia Pituach (IL)

(72) Inventor: Nir Regev, Barkan (IL)

(73) Assignee: Essence Smartcare Ltd., Herzlia Pituach (IL)

( * ) Notice: Subject to any disclaimer, the term of this patent is extended or adjusted under 35 U.S.C. 154(b) by 266 days.

(21) Appl. No.: 16/099,458

(22) PCT Filed: May 9, 2017

(86) PCT No.: PCT/IL2017/050510
§ 371 (c)(1),
(2) Date: Nov. 7, 2018

(87) PCT Pub. No.: WO2017/195196
PCT Pub. Date: Nov. 16, 2017

(65) Prior Publication Data
US 2019/0183352 A1 Jun. 20, 2019

Related U.S. Application Data

(60) Provisional application No. 62/439,065, filed on Dec. 26, 2016, provisional application No. 62/333,298, filed on May 9, 2016.

(51) Int. Cl.
*A61B 5/0205* (2006.01)
*G01S 7/41* (2006.01)
(Continued)

(52) U.S. Cl.
CPC ............ *A61B 5/0205* (2013.01); *A61B 5/002* (2013.01); *A61B 5/024* (2013.01); *A61B 5/04* (2013.01);
(Continued)

(58) Field of Classification Search
None
See application file for complete search history.

(56) References Cited

U.S. PATENT DOCUMENTS 8,781,563 B2   7/2014   Foo
8,834,364 B2   9/2014   Heneghan et al.
(Continued)

FOREIGN PATENT DOCUMENTS

WO   WO 2017/195196   11/2017

OTHER PUBLICATIONS

Communication Pursuant to Article 94(3) EPC dated Jul. 14, 2020 From the European Patent Office Re. Application No. 17795738.8. (12 Pages).

(Continued)

*Primary Examiner* — Michael W Kahelin

(57) ABSTRACT

A system for estimating breathing frequency and heartbeat frequency of a subject, comprises at least one ultra-wideband (UWB) transceiver, connected to at least one hardware processor, configured to: receive a plurality of readings from the UWB transceiver, each of the readings having a time and comprising a plurality of intensity values at the time, each of the intensity values having a corresponding distance value representing a distance between the UWB transceiver and the subject; determine a Range-Doppler map from the plurality of readings; analyze the Range-Doppler map to determine a breathing frequency value of the subject; perform null steering of a plurality of Doppler-map frequencies in the Range-Doppler map to nullify the breathing frequency value and integer multiples of the breathing frequency value to obtain a plurality of combined frequencies; and determine a heartbeat frequency value for which a plurality of computed frequencies corresponds with the plurality of combined frequencies.

19 Claims, 6 Drawing Sheets

(51) Int. Cl.

| | |
|---|---|
| *A61B 5/05* | (2006.01) |
| *A61B 5/08* | (2006.01) |
| *G01S 13/02* | (2006.01) |
| *A61B 5/00* | (2006.01) |
| *A61B 5/04* | (2006.01) |
| *A61B 5/113* | (2006.01) |
| *G01S 13/536* | (2006.01) |
| *A61B 5/024* | (2006.01) |
| *A61B 5/11* | (2006.01) |

(52) U.S. Cl.
CPC .......... *A61B 5/0507* (2013.01); *A61B 5/0816* (2013.01); *A61B 5/113* (2013.01); *A61B 5/7257* (2013.01); *G01S 7/414* (2013.01); *G01S 7/415* (2013.01); *G01S 13/0209* (2013.01); *G01S 13/536* (2013.01); *A61B 5/02444* (2013.01); *A61B 5/11* (2013.01); *A61B 5/1115* (2013.01); *A61B 5/742* (2013.01); *A61B 5/7405* (2013.01); *A61B 2562/0228* (2013.01); *A61B 2562/046* (2013.01); *A61B 2562/166* (2013.01)

(56) References Cited

U.S. PATENT DOCUMENTS

| | | | |
|---|---|---|---|
| 2010/0026550 | A1 | 2/2010 | Rosenbury |
| 2014/0378809 | A1 | 12/2014 | Weitnauer et al. |

OTHER PUBLICATIONS

Supplementary European Search Report and the European Search Opinion dated Nov. 29, 2019 From the European Patent Office Re. Application No. 17795738.8. (15 Pages).

Bugaev et al. "Radar Methods of Detection of Human Breathing and Heartbeat", Journal of Communications Technology and Electronics, XP019439400, 51(10): 1154-1168, Oct. 2006.

Chen "Advances in Applications of Radar Micro-Doppler Signatures", 2014 IEEE Conference on Antenna Measurements & Applications, CAMA, Antibes Juan-le-Pins, France, Nov. 16-19, 2014, XP032718324, p. 1-4, Nov. 16, 2014.

Khunti "Vital Sign Estimation Through Doppler Radar", A Thesis Presented in Partial Fulfillment of the Requirements for the Degree of Master of Science, Arizona State University, USA, XP055643460, p. 1-57, Aug. 2013.

Lan et al. "Life-Sign Detection of Through-Wall-Radar Based on Fourth-Order Cumulant", 2013 IEEE Radar Conference, Radar Con13, Ottawa, Ontario, Canada, Apr. 29-May 3, 2013, XP032479633, p. 1-4, Apr. 29, 2013.

Lazaro et al. "Analysis of Vital Signs Monitoring Using an IR-UWB Radar", Progess in Electromagnetics Research, PIER, XP002593852, 100: 265-284, Jan. 2010.

Leib et al. "Vital Signs Monitoring With a UWB Radar Based on a Correlation Receiver", 2012 Proceedings of the Fourth European Conference on Antennas and Propagation, EUCAP, Barcelona, Spain, Apr. 12-16, 2012, XP031705399, p. 1-5, Apr. 12, 2012.

Shirodkar et al. "Heart-Beat Detection and Ranging Through a Wall Using Ultra Wide Band Radar", International Conference on Communications and Signal Processing, ICCSP, Calicut, India, Feb. 10-12, 2011, XP031932655, p. 579-583, Feb. 10, 2011.

International Preliminary Report on Patentability dated Nov. 22, 2018 From the International Bureau of WIPO Re. Application No. PCT/IL2017/050510. (6 Pages).

International Search Report and the Written Opinion dated Aug. 8, 2017 From the International Searching Authority Re. Application No. PCT/IL2017/050510. (10 Pages).

SYSTEM AND METHOD FOR ESTIMATING VITAL SIGNS

BACKGROUND

The present invention, in some embodiments thereof, relates to a system for estimating vital signs of a subject and, more specifically, but not exclusively, to a system for estimating a breathing frequency and heartbeat frequency of a person.

It happens that vital signs, for example a breathing frequency or a heartbeat frequency, of a person of young or old age or poor health degrades during times when the person is not monitored by another person, for example when the person is asleep. While appropriate care could save the person's life, it happens that such help does not arrive until it is too late to prevent the person's death. There is a need to monitor a person's vital signs continuously.

There exist wearable devices to provide continuous indications of a person's condition. Such wearable devices may alert when a deviation in a vital sign is observed, for example when there is a decrease in breath frequency or heartbeat frequency. However, such wearable devices disturb some persons; some persons are inconvenienced by wearing such wearable devices.

SUMMARY

It is an object of the present invention to provide a system and a method for monitoring vital signs of a subject.

The foregoing and other objects are achieved by the features of the independent claims. Further implementation forms are apparent from the dependent claims, the description and the figures.

According to a first aspect of the present invention, a system for estimating breathing frequency and heartbeat frequency of a subject comprises at least one ultra-wideband (UWB) transceiver, connected to at least one hardware processor, configured to: receive a plurality of return signal readings from said UWB transceiver, each of the readings having a time and comprising a plurality of intensity values at the time, each of the intensity values having a corresponding distance value representing a distance between the UWB transceiver and the subject; determine a Range-Doppler map from the plurality of return signal readings; analyze the Range-Doppler map to determine a breathing frequency value of the subject; perform null steering of a plurality of Doppler-map frequencies in the Range-Doppler map to nullify the breathing frequency value and integer multiples of the breathing frequency value, to obtain a plurality of combined frequencies comprising a plurality of harmonies of a heartbeat frequency and a plurality of other frequencies, each a sum of an integer multiple of the breathing frequency value and another integer multiple of one of the plurality of harmonies, or a difference between an integer multiple of the breathing frequency value and another multiple of one of the plurality of harmonies; and determine a heartbeat frequency value for which a plurality of computed frequencies corresponds with the plurality of combined frequencies, wherein the plurality of computed frequencies comprises a plurality of computed harmonies of the determined heartbeat frequency and a plurality of other computed frequencies, each being a sum of an integer multiple of the breathing frequency value and another integer multiple of one of the plurality of computed harmonies, or a difference between an integer multiple of the breathing frequency value and another multiple of one of the plurality of computed harmonies. A UWB transceiver typically emits low power, making it suitable to use in a typical room to monitor a person. Nullifying the breathing frequency from the Range-Doppler map enables determining the heartbeat frequency by solving a simple optimization problem.

According to a second aspect of the present invention, a method for estimating breathing frequency and heartbeat frequency of a subject comprises receiving a plurality of return signal readings from a UWB transceiver, each of the readings having a time and comprising a plurality of intensity values at the time, each of the intensity values having a corresponding distance value representing a distance between the UWB transceiver and the subject; determining a Range-Doppler map from the plurality of return signal readings; analyzing the Range-Doppler map to determine a breathing frequency value of the subject; performing null steering of a plurality of Doppler-map frequencies in the Range-Doppler map to nullify the breathing frequency value and integer multiples of the breathing frequency value, to obtain a plurality of combined frequencies comprising a plurality of harmonies of a heartbeat frequency and a plurality of other frequencies, each a sum of an integer multiple of the breathing frequency value and another integer multiple of one of the plurality of harmonies, or a difference between an integer multiple of the breathing frequency value and another multiple of one of the plurality of harmonies; and determining a heartbeat frequency value for which a plurality of computed frequencies corresponds with the plurality of combined frequencies, wherein the plurality of computed frequencies comprises a plurality of computed harmonies of the determined heartbeat frequency and a plurality of other computed frequencies, each a sum of an integer multiple of the breathing frequency value and another integer multiple of one of the plurality of computed harmonies, or a difference between an integer multiple of the breathing frequency value and another multiple of one of the plurality of computed harmonies.

With reference to the first and second aspects, in a first possible implementation of the first and second aspects of the present invention, the transceiver is an impulse radio transceiver. Impulse transceivers provide continuous readings, for continuous monitoring.

With reference to the first and second aspects, in a second possible implementation of the first and second aspects of the present invention, the at least one hardware processor is further configured to analyze the Range-Doppler map to determine a breathing frequency value of the subject comprising: identifying at least one peak frequency in the Range-Doppler map; performing spectral estimation of each of the at least one peak frequency to obtain at least one sequence of harmonies, each comprising for one of the at least one peak frequency a first harmony frequency, a second harmony frequency and a third harmony frequency of the at least one peak frequency; and determining a breathing frequency value as a difference between frequency values of two consecutive peaks of the at least one sequence of harmonies. Performing spectral estimation comprises applying Multiple Signal Classification (MUSIC) or Fast Fourier Transform (FFT) to at least one row of said Range-Doppler map representing a distance having that at least one peak frequency. Peaks in the Range-Doppler map correspond to distances at which a subject is detected, and spectral frequencies of these peaks correspond with frequencies of the subject's breathing and heartbeat, so those peaks are analyzed. FFT is a common and efficient method for performing spectral analysis; MUSIC is effective in distinguishing close harmonies.

With reference to the first and second aspects, in a third possible implementation of the first and second aspects of the present invention, the at least one hardware processor is further configured to perform null steering of the plurality of Doppler frequencies using MUSIC with spectral nulling. MUSIC is an effective method of performing null steering.

With reference to the first and second aspects, in a fourth possible implementation of the first and second aspects of the present invention, the at least one hardware processor is further configured to determine the Range-Doppler map from the plurality of return signal readings comprising: canceling clutter with regard to intensity from each of the plurality of return signal readings, to produce a plurality of intensity-cleaned processed readings; producing a plurality of bins by partitioning a distance axis of the plurality of return signal readings into an identified amount of bins; canceling clutter with regard to distance from each of the plurality of intensity-cleaned readings to produce a plurality of distance-cleaned readings; for each of the plurality of bins, multiplying all intensity values in said plurality of distance-cleaned readings associated with the bin's distances by a window function in time domain to produce a plurality of windowed readings; applying to the plurality of windowed readings a frequency filter for an identified range of frequencies to eliminate frequencies not relevant to breathing or heartbeat frequencies, to produce a plurality of filtered readings; and applying FFT to each of the plurality of filtered readings to produce a Range-Doppler map. The window function is a Hann function window. The identified range of frequencies is between 0.1 Hertz and 4 Hertz. Cancelling clutter with regard to intensity from each of the plurality of return signal readings comprises: computing an average intensity value of the plurality of intensity values of the reading; and subtracting the average intensity value from each of the plurality of intensity values of the reading. Cancelling clutter with regard to distance from each of the plurality of intensity-cleaned readings comprises computing for each distance a second average intensity value of the plurality of intensity values of all of the plurality of intensity-cleaned readings corresponding with the distance, and subtracting the second average intensity value from each of the plurality of intensity values of all of the plurality of intensity-cleaned readings corresponding with the distance. Cleaning clutter produces a Range-Doppler map better representing the breathing frequency and heartbeat frequency of the subject. Partitioning the distance axis into a plurality of bins and applying a window function to each bin of the plurality of bins eliminates interferences between signals detected at different distances. Filtering the frequencies eliminates frequencies that are irrelevant to breathing and heartbeat.

With reference to the first and second aspects, in a fifth possible implementation of the first and second aspects of the present invention, the at least one hardware processor is further configured to: send a message to a control hardware processor, subject to a produced breathing frequency value deviating in at least a predetermined threshold from a reference frequency, wherein the reference frequency is selected from the group consisting of: a previously produced breathing frequency and a predetermined reference breathing frequency. Optionally, the predetermined threshold is a relative difference between the produced breathing frequency and the reference frequency, for example 5 percent of the reference frequency. Optionally, the predetermined threshold is an amount of Hertz. Respiratory problems may manifest as a relative change (increase or decrease) in breathing frequency or an absolute increase or decrease in breathing frequency above or below a predetermined threshold, respectively.

With reference to the first and second aspects, in a sixth possible implementation of the first and second aspects of the present invention, the at least one hardware processor is further configured to: send a message to a control hardware processor, subject to a produced heartbeat frequency value deviating in at least a predetermined heartbeat difference threshold from a reference frequency, wherein the reference frequency is selected from the group consisting of: a previously produced heartbeat frequency and a predetermined reference heartbeat frequency. Optionally, the predetermined threshold is a relative difference between the produced heartbeat frequency and the reference frequency, for example 5 percent of the reference frequency. Optionally, the said predetermined threshold is an amount of Hertz. Heartbeat problems may manifest as a relative change (increase or decrease) in heartbeat frequency or an absolute increase or decrease in heartbeat frequency above or below a predetermined threshold, respectively.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
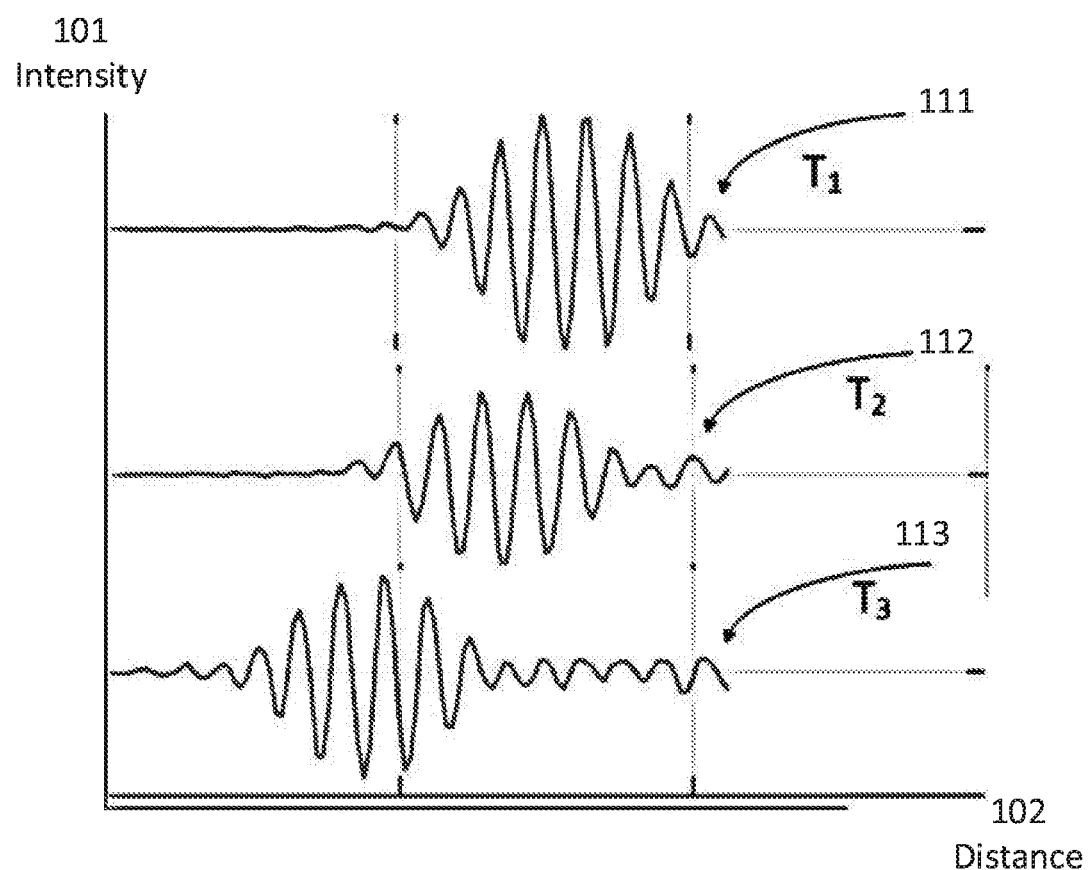
FIG. 1 is graph representations of three exemplary return signal readings.

The present invention, in some embodiments thereof, relates to a system for estimating vital signs of a subject and, more specifically, but not exclusively, to a system for estimating a breathing frequency and heartbeat frequency of a person.

Remote vital signs monitoring and tracking are of importance for various applications including, but not limited to, infant care, elderly care, human activity behind barriers, and bio-medical applications. Wearable devices providing continuous indications of a person's condition exist, but some persons are disturbed by such devices and find them uncomfortable.

A radar transmits a radio frequency (RF) signal and receives an echo signal (also called a return signal) of the RF signal from multiple targets in its search volume. A typical radar system analyzes the return signal to detect multiple targets in its search volume and determine at what distance each target is detected. The distance at which radar aimed at a thorax of a person detects the changes in location of the person's thorax due to breathing and heartbeat movements. Whenever a target undergoes micro-motion dynamics, such as vibrations and rotations, the return signal is frequency modulated, an effect referred to as the micro-Doppler (uDoppler) effect. Harmonic movement of a person's thorax due to the heart beat and respiration causes this frequency modulation effect on the return signal. The frequency modulation in the return signal may be analyzed for estimating a breathing frequency and/or a heartbeat frequency.

An ultra-wideband (UWB) frequency is currently defined by the International Telecommunication Union Radiocommunication Sector as an antenna transmission for which emitted signal bandwidth exceeds the lesser of 500 Megahertz (MHz) or 20% of the arithmetic center frequency of the emitted signal. Range resolution is the ability of a radar system to distinguish between two or more targets on the same bearing but at different ranges. Radar using UWB frequencies has a wide bandwidth which yields a high range resolution, so it is suitable for short ranges such as in a typical room, for example of a room having an area of approx. 12 square meters. The high range resolution also makes radar using UWB frequencies suitable for detecting both breathing and heartbeat simultaneously. In addition, radar using UWB typically has very low emitted power, another advantage when using a radar in a typical room, and in the vicinity of people. However, in wide bandwidth non-linear pulses typically used by such radar, some spectral components of signals returned by objects in the radar's search volume become inter-modulated, introducing into the return signal received by the radar spectral components at frequencies that are not integral multiples of the spectral components of the signals returned by the objects. As a result, typical radar processing of Discrete Fourier Transform (DFT) using Fast Fourier Transform (FFT) is insufficient for differentiating close proximity spectral components of the returned signal. When a radar transceiver is aimed at a thorax of a person, the returned signal spectrum includes the person's heartbeat fundamental and respiration (breathing) fundamental frequencies and their corresponding integer multiplicity harmonies, as well as their mutual inter-modulation frequencies. These mutual inter-modulation frequencies pose a difficulty in extracting the correct heartbeat fundamental frequency.

Typically, a person's heartbeat frequency and the person's breathing frequency are non-synchronized. In addition, the cycle length of the person's breathing may contain an integer number of cycle lengths of the person's heartbeat but does not necessarily do so. In addition, the amount of cycle lengths of the person's heartbeat contained in the cycle length of the person's breathing typically varies over time. Both these frequencies contribute to the change in location of where the person is detected, however the amplitude of the person's heartbeat frequency is negligible relative to the amplitude of the person's breathing frequency in these two frequencies inter-modulated with each other, resulting in various nuisance interferences in super-position of both these frequencies and their integer multiples.

In addition, a person's breathing frequency typically has harmonies which are close in frequency to the heartbeat frequency but have higher energy, making it even more difficult to separate the two frequencies. The present invention, in some embodiments thereof, processes the combined return signal in order to filter out the breathing signal while leaving the heartbeat signal.

As used henceforth, a Range-Doppler map is a matrix of values representing one or more waveforms in the frequency domain with regard to a plurality of distances.

In the current invention, in some embodiments thereof, after detecting a breathing frequency from a Range-Doppler map, the detected breathing frequency and its integer multiples are nullified from the waveforms represented by the Range-Doppler map, leaving a plurality of values representing one or more waveforms having factors that are integer multiples of a yet unknown heartbeat frequency, or an integer multiple of the breathing frequency value and another integer multiple of the yet unknown heartbeat frequency, or a difference between an integer multiple of the breathing frequency value and another multiple of the yet unknown heartbeat frequency.

Null steering (also known as zero-cancelling) is a method for considering an impact on a background signal and an unknown interference signal, where the background signal and the unknown interference signal can be emphasized in the result of (known) interference nulling. The current invention, in some embodiments thereof, applies null steering to a plurality of values in a matrix of values representing one or more waveforms, to nullify the detected breathing frequency and its integer multiples from the waveforms represented by the Range-Doppler map, leaving a plurality of values representing one or more waveforms having factors that are integer multiples of a yet unknown heartbeat frequency, or an integer multiple of the breathing frequency value and another integer multiple of the yet unknown heartbeat frequency, or a difference between an integer multiple of the breathing frequency value and another multiple of the yet unknown heartbeat frequency.

After eliminating the detected breathing frequencies, some embodiments of the present invention solve a cost function optimization problem to determine a heartbeat frequency value having a highest probability of yielding the peaks in the Range-Doppler map.

Optionally, an autocorrelation matrix is used instead of a Range-Doppler map. An autocorrelation matrix may be produced by computing a plurality of autocorrelation computations, each autocorrelation computation computed using a plurality of intensity values associated with an identified range of distances from the UWB transceiver, collected over a period of time. After detecting a breathing frequency, the detected breathing frequency and its integer multiples may be nullified from the waveforms represented by the autocorrelation matrix, and a cost function optimization problem may be solved to determine a heartbeat frequency value having a highest probability of yielding the peaks in the autocorrelation matrix.

The current invention has an advantage over typical UWB radar processing in that it allows distinguishing between a breathing frequency and a heartbeat frequency even in return signals of UWB frequencies, enjoying the benefits of UWB radar technology's low power emission and high range resolution in vital sign monitoring and detection.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A typical radar transceiver transmits a signal and receives a return signal every predetermined period of time, for example between 5 and 50 times a second. Every return signal is a reading, and may be depicted as a graph indicating the return signal's intensity in relation to a distance from the transceiver.

Reference is now made to FIG. 1, showing graph representations of three exemplary return signal readings. A reading of a return signal of a transceiver aimed at a thorax of a person received at an identified time T1 is represented by graph 111, showing return signal intensity values in relation to distance from the transceiver. X-axis 102 represents distance from the transceiver; Y-axis 101 represents intensity of the return signal. A reading of a second return signal received at a second identified time T2 is represented by graph 112, a reading of a third return signal received at a third identified time T3 is represented by graph 113. Times T1, T2 and T3 are different times.

Figure 2:
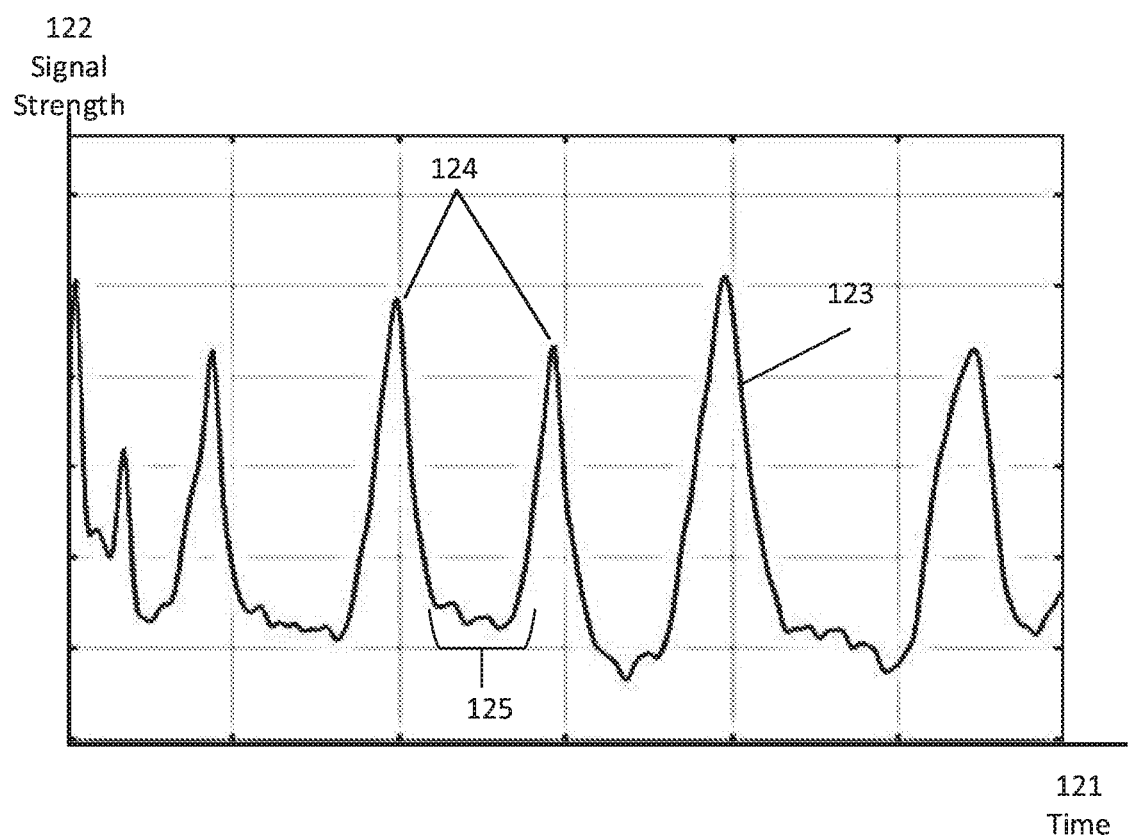
FIG. 2 is a graph representation of signal strength in relation to time at an identified distance of an exemplary combined heartbeat and breathing signal.

Reference is now made also to FIG. 2, showing a graph representation 123 of signal strength in relation to time at an identified distance of an exemplary combined heartbeat and breathing signal. X-axis 121 represents time; Y-axis 122 represents signal strength. Points 124 are two peaks corresponding with a frequency of the person's breathing frequency. Range 125, between two breathing peaks, demonstrates fluctuations corresponding with a frequency of the person's heartbeat frequency. The person's heartbeat frequency is present in parts of the graph other than breathing lows between two peaks, however the person's heartbeat frequency is typically unnoticeable due to large variations in thorax position during most of the breathing cycle, and is noticeable almost only when the chest is at rest, between breaths.

The present invention, in some embodiments thereof, separates a breathing frequency component and a heartbeat frequency component of a combined heartbeat and breathing signals of a person, such as the signal shown in FIG. 2, using a plurality of return signal readings such as shown in FIG. 1.

Figure 3:
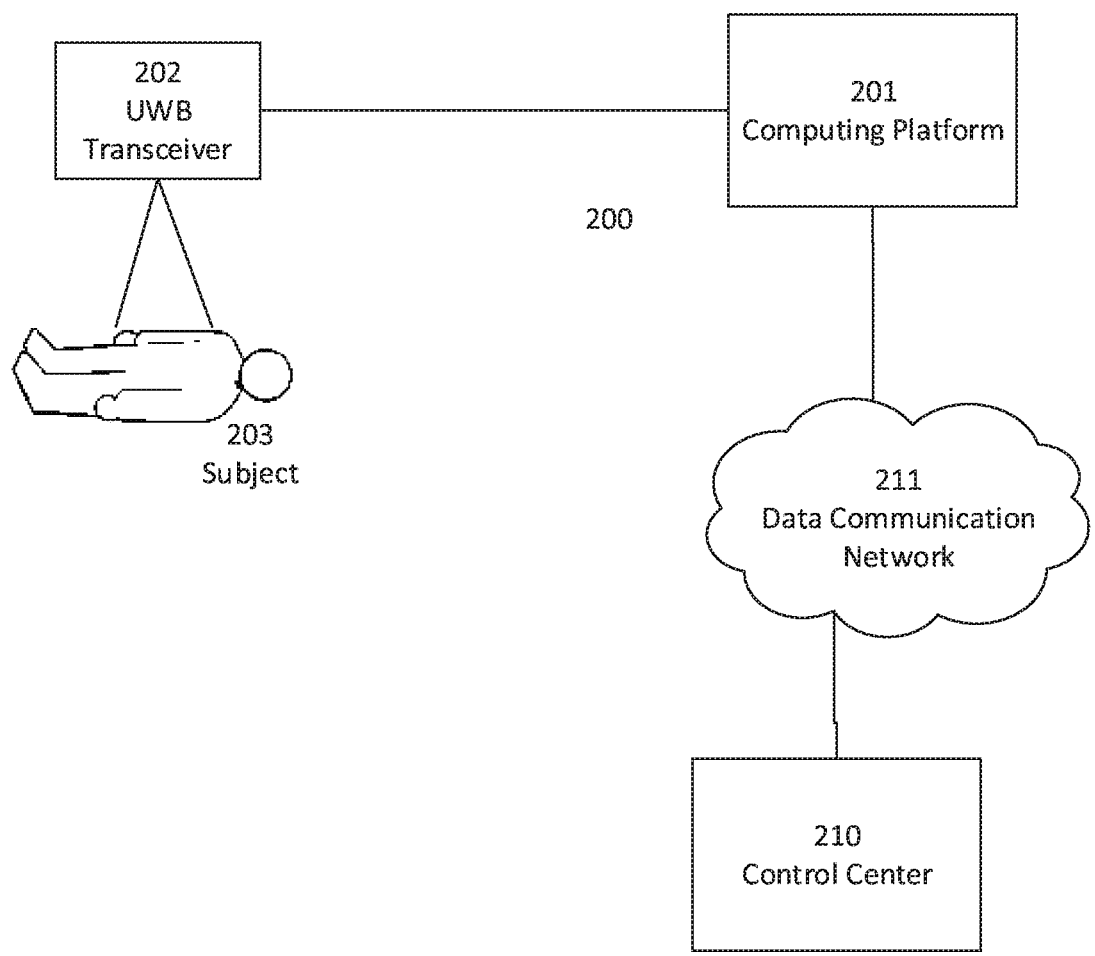
FIG. 3 is a schematic block diagram of an exemplary system according to some embodiments of the present invention.

Reference is now made also to FIG. 3, showing a schematic block diagram of an exemplary system 200 for detecting a breathing frequency and a heartbeat frequency using an UWB transceiver, according to some embodiments of the present invention. In such embodiments, the system comprises a UWB transceiver 202, aimed at a thorax of a monitored person 203. A typical UWB transceiver has a low emitting power, for example in the range of −10.0 to −20.0 decibel-milliwatts. Optionally, the transceiver is a UWB impulse radar transceiver. For example, a Novelda X2 XETHRU radar, having a low emitting power in the range of −10.5 to −15.1 decibel-milliwatts. The transceiver may be a single transmitter/single receiver UWB impulse radar transceiver.

In such embodiments, UWB transceiver 202 sends a plurality of return signal readings to a computing platform 201 electrically connected to UWB transceiver 202. Computing platform 201 comprises at least one hardware processor. Optionally, the plurality of return signal readings has several hundred readings, for example 100 or 256 readings. Optionally, the plurality of return signal readings has several thousand readings, for example 2048 or 4096 readings.

In some embodiments, computing platform 201 is connected to a control center 210 via a data communication network 211 such as a Local Area Network (LAN) or a Wide Area Network (WAN). Optionally, data communication network 211 is an Internet Protocol (IP) network. Optionally, data communication network 211 is a wireless network. Control center 210 comprises at least one hardware processor, adapted to receive messages from the computing platform via the data communication network. In some embodiments computing platform 201 determines the monitored person's breathing frequency and heartbeat frequency and sends the determined frequencies to control center 210 via data communication network 211. Optionally, computing platform 201 sends the plurality of return signal readings to control center 210 and control center 210 determines the monitored person's breathing frequency and heartbeat frequency from the readings.

Control center 210 may be local to computing platform 201, that is located in the same premises as computing platform 201, or may be remote, that is located in different premises than computing platform 201. Optionally, control center 210 is electrically connected to a device capable of emitting an audio signal such as an alarm sound or a visual signal, such as a flashing light, for the purpose of drawing the attention of a designated person monitoring the system, and located close enough to control center 210 to see a visual signal or hear an audio signal. Control center 210 may determine that a change has occurred in one or more of the determined frequencies, for example, a value of one of the determined frequencies increased or dropped more than a predetermined threshold. The predetermined threshold may be a percentage of a predetermined reference frequency, for example 5% or 10% of the predetermined reference frequency. The predetermined threshold may be an absolute amount, for example an amount of Hertz. Upon determining a change, control center 210 may deliver an electrical signal to the device capable of emitting an audio signal or a visual signal. Optionally, upon determining a change, control center 210 calls the monitored person, calls a family member of the monitored person, calls a care giver of the monitored person or takes another action.

In some embodiments of the present invention, UWB transceiver 202 continuously sends return signal readings to computing platform 201, for continuous monitoring of the monitored person's vital signs. For example UWB transceiver 202 may send computing platform 201 a plurality of return signal readings every 50-100 milliseconds. Optionally, UWB transceiver 202 stops sending readings to computing platform 201 when no motion is sensed, for example because the monitored person woke up and moved away from the search volume of UWB transceiver 202, optionally after giving a notice. Optionally, UWB transceiver 202 stops sending readings to computing platform 201 upon receiving an instruction from a person.

To provide a solution for determining a breathing frequency and a heartbeat frequency of a monitored subject, in some embodiments of the present invention the systems implement the following method.

Figure 4:
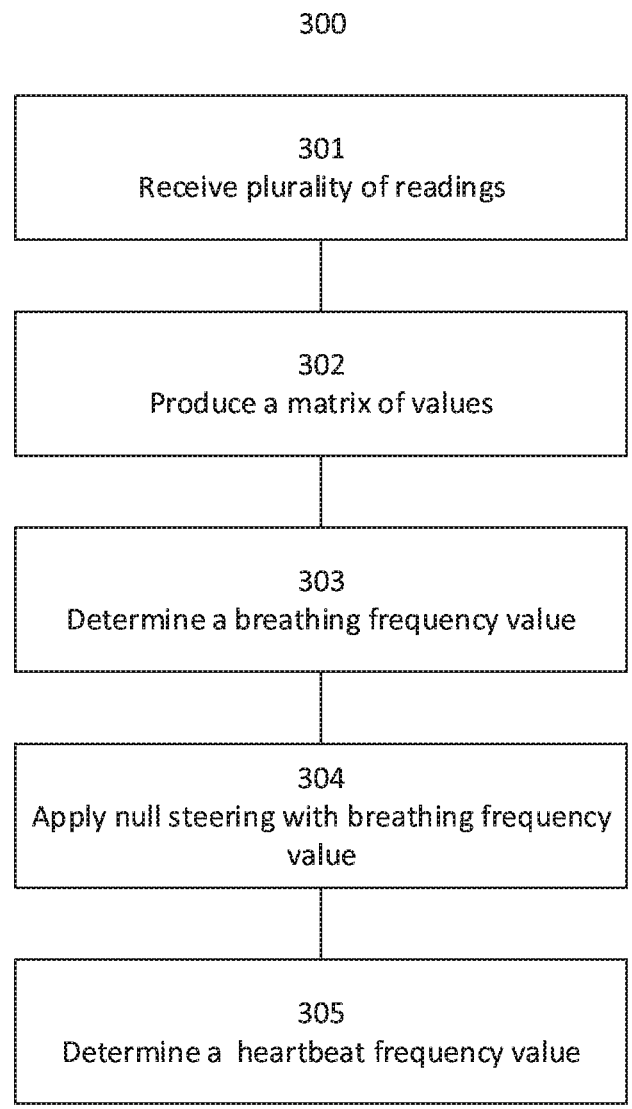
FIG. 4 is a flowchart schematically representing an optional flow of operations for determining a breathing frequency and a heartbeat frequency of a monitored subject, according to some embodiments of the present invention.

Reference is now made also to FIG. 4, showing a flowchart schematically representing an optional flow of operations 300 for determining a breathing frequency and a heartbeat frequency of a monitored subject, according to some embodiments of the present invention.

First, as shown at 301, a computing platform receives a plurality of return signal readings from a UWB transceiver. Each of the return signal readings comprises a time and a plurality of intensity values detected by the UWB transceiver at the time. Each of the intensity values has a corresponding distance value, representing a distance between the UWB transceiver and the subject. Each of the plurality of readings has a different time. Optionally, the plurality of return signal readings are received at once. Optionally, the plurality of return signal readings are received over a period of time, for example over 30 seconds.

Now, as shown at 302, the computing platform produces a matrix of values from the plurality of readings. A possible method for producing the matrix of values is now described.

Figure 5:
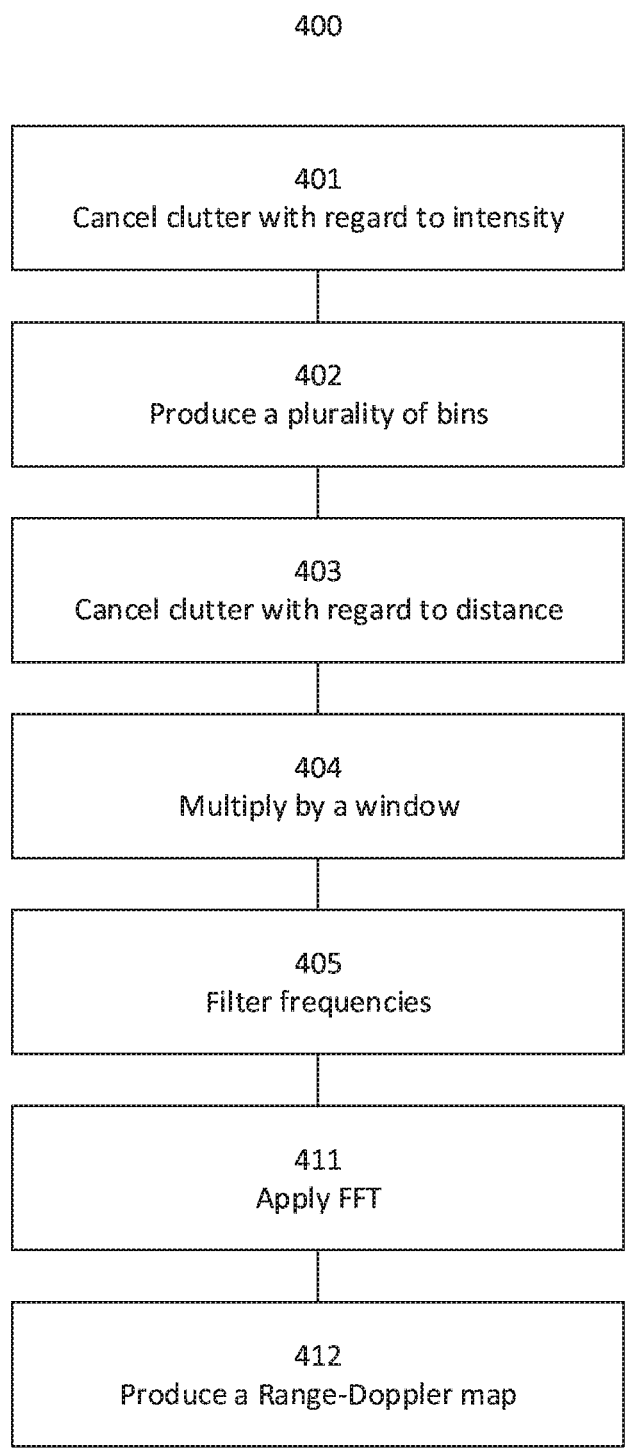
FIG. 5 is a flowchart schematically representing an optional flow of operations for producing a matrix of values, according to some embodiments of the present invention.

Reference is now made also to FIG. 5, showing a flowchart schematically representing an optional flow of operations 400 for producing a matrix of values, according to some embodiments of the present invention. In such embodiments, in 401 the computing platform performs clutter cancellation with regard to intensity for each of the plurality of readings. Optionally, clutter cancellation with regard to intensity for one reading is done by computing an average intensity value of the plurality of intensity values of the reading and subtracting the average intensity value from each of the plurality of intensity values of the reading. Such a computation shifts the plurality of intensity values closer to zero. Graphically, the plurality of intensity values are moved close to an X-axis in a graph representation of the reading. The result of clutter cancellation for the plurality of readings is a plurality of intensity-cleaned readings.

Optionally, in 402 the computing platform produces a plurality of bins, each bin comprising a plurality of distance values, by partitioning a plurality of distance values corresponding to the plurality of intensity values into an identified predetermined amount of bins. For example, in a system where a reading comprises intensity values corresponding with distances between 0-1 meters, the plurality of distance values may be partitioned into 256 bins, each representing a range of distances of approx. 4 millimeters. Next, in such embodiments, in 403 the computing platform performs clutter cancellation with regard to distance for each of the plurality of intensity-cleaned readings. Optionally, clutter cancellation with regard to distance for each of the plurality of intensity-cleaned readings is done by computing for each distance a second average intensity value of the plurality of intensity values of all of the plurality of intensity-cleaned readings corresponding to the distance and subtracting the second average intensity value from each of the plurality of intensity values of all of the plurality of intensity-cleaned readings corresponding with the distance. Such a computation shifts the plurality of intensity values closer to zero. Graphically, the plurality of intensity values are moved close to a Y-axis in a representation of the processed reading. The result of clutter cancellation for the plurality of intensity-cleaned readings is a plurality of distance-cleaned readings.

Optionally, in 404, the computing platform multiplies, for each of the plurality of bins, all intensity values in the plurality of distance-cleaned readings associated with the bin's distances by a window function in time domain to produce a plurality of windowed readings. Multiplying by a window function eliminates transition effects between segments of a reading, and leaves only the center intensity values corresponding with each bin of distances. Optionally, the window function is a Hann function window in the time domain. Using a square window is possible, however may cause spectral leakage between some of the plurality of bins, where a sinusoid representation of the intensity values of one bin is influenced by intensity values of another bin. A Hann function window is graded, causing less spectral leakage between some of the plurality of bins.

Optionally, in 405, the computing platform applies to the plurality of windowed readings a frequency filter for an identified range of frequencies, to eliminate frequencies irrelevant to breathing or heartbeat frequencies, to produce a plurality of filtered readings. For example, the frequency range may be between 0.1-4 Hertz. Optionally, the frequency filter is a high pass and low pass filter.

Next, in such embodiments the computing platform produces a matrix of values. Optionally, the matrix of values is a Range-Doppler map, having a plurality of frequency coefficients.

In embodiments where the matrix of values is a Range-Doppler map, the computing platform applies FFT 411 to each of the plurality of filtered readings, and combines the results to produce 412 a Range-Doppler map, having a frequency dimension and a distance dimension. Optionally the frequency dimension is an X-axis of the matrix of values, and the distance dimension is the Y-axis of the matrix of values. Each value in such a Range-Doppler map may represent an intensity value detected by the UWB transceiver at the respective distance from the UWB transceiver at the respective frequency.

Referring again to FIG. 4, the computing platform now determines 303 a breathing frequency value from the matrix of values. This is done by identifying peaks in the matrix of values, performing spectral estimation of the peaks and calculating a breathing frequency value using the results of the spectral estimation. A possible method for determining a breathing frequency from the matrix of values is now described.

Figure 6:
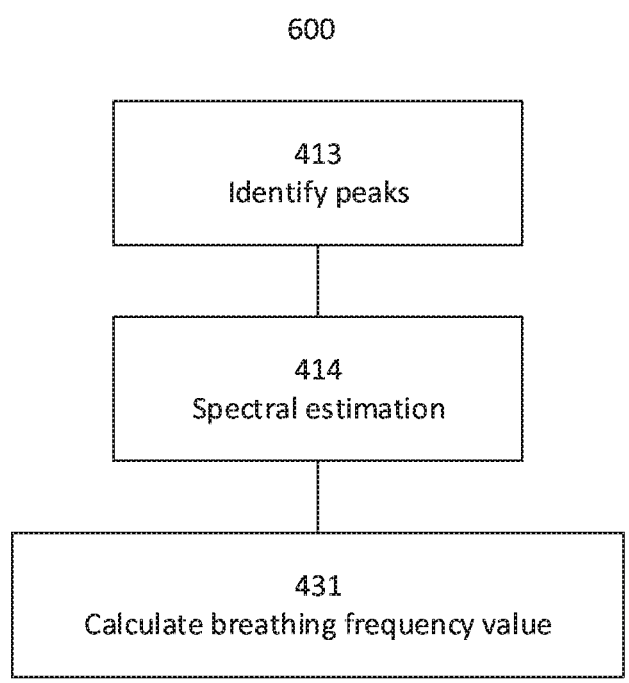
FIG. 6 is a flowchart schematically representing an optional flow of operations for determining a breathing frequency, according to some embodiments of the present invention.

Reference is now made also to FIG. 6, showing a flowchart schematically representing an optional flow of operations 600 for determining a breathing frequency, according to some embodiments of the present invention. First the computing platform identifies 413 at least one peak value in the matrix of values and performs spectral estimation 414 of the at least one peak value to obtain at least one sequence of harmonies, each comprising for one of the at least one peak frequency a first harmony frequency, a second harmony frequency and a third harmony frequency of the one of the at least one peak value. In embodiments where the matrix of values is a Range-Doppler map, the at least one peak value is at least one peak frequency. In such embodiments, the computing platform identifies at least one peak frequency in the Range-Doppler map, and performs spectral estimation of the at least one peak frequency In a typical radar system, at least one peak frequency is found for a frequency which is a multiple of the velocity of the subject. In some embodiments, the at least one peak frequency is a multiple of a velocity of the subject's thorax with a predetermined scalar. Optionally, the spectral estimation is by applying Multiple Signal Classification (MUSIC) to at least one row of the Range-Doppler map representing a distance having the at least one peak frequency. MUSIC is typically used for estimating direction; here it is used for estimating a spectrum of a reading. Optionally, the spectral estimation is by applying FFT to the at least one row of the Range-Doppler map representing a distance having the at least one peak frequency.

After performing spectral estimation, a breathing frequency may be determined from the at least one sequence of harmonies. Optionally, in 431 the computing platform calculates a breathing frequency value by calculating a difference between frequencies of two consecutive peaks in the at least one sequence of harmonies.

Now a heartbeat frequency may be determined.

A heartbeat has a higher frequency and lower intensity than respective frequency and intensity of breathing. The heartbeat frequency and its harmonies are close to the breathing frequency. For example, when the breathing frequency is denoted by $f_b$ and the heartbeat frequency is denoted by $f_h$, the matrix of values contains peaks corresponding to frequencies equal to $f_b+f_h$, $f_b-f_b$, $2*f_b+f_h$, $2*f_b-f_h$, $3*f_b+f_h$, $3*f_b-f_h$, $f_b+f_h$, $3*f_b-2f_b$, $3*f_b-2*f_b$, and additional combinations of the breathing and heartbeat frequencies. Null steering may be performed to eliminate the breathing frequency component from the peaks in the matrix of values.

Referring again to FIG. 4, in some embodiments the computing platform applies null steering 304 to the matrix of values to nullify the breathing frequency value and integer multiples of the breathing frequency value, to obtain a plurality of combined frequencies comprising peak frequencies that are not the breathing frequency and its integer multiples. In such embodiments, the plurality of combined frequencies comprises a plurality of harmonies of a heartbeat frequency and a plurality of other frequencies, each a sum of an integer multiple of the breathing frequency value and another integer multiple of one of the plurality of harmonies, or a difference between an integer multiple of the breathing frequency value and another multiple of one of the plurality of harmonies. Optionally, null steering is performed by applying MUSIC with spectral nulling to the matrix of values and the breathing frequency. Prior to applying MUSIC with spectral nulling, a new matrix of values may be produced using a window function with a narrower time than used to produce the matrix of values, in order to obtain high frequencies, for example above 1 Hertz; then MUSIC with spectral nulling is applied to the new matrix to obtain the plurality of combined frequencies.

In some embodiments the computing platform solves an optimization problem using the breathing frequency and the plurality of combined frequencies to determine 305 a heartbeat frequency value most likely to yield the peaks in the matrix of values corresponding to the plurality of combined frequencies. Solving the optimization problem may be done by a one dimensional optimization extracting a most likely heartbeat frequency value, such that a plurality of computed frequencies, comprising a plurality of computed harmonies of the determined heartbeat frequency and a plurality of other computed frequencies, each being a sum of an integer multiple of the breathing frequency value and another integer multiple of one of the plurality of computed harmonies, or a difference between an integer multiple of the breathing frequency value and another multiple of one of the plurality of computed harmonies corresponds with the plurality of combined frequencies.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant null steering methods will be developed and the scope of the term "null steering" is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for determining heartbeat frequency of a subject, comprising:
   at least one ultra-wideband (UWB) transceiver, connected to at least one hardware processor, configured to:
   receive a plurality of return signal readings from said UWB transceiver, each of said readings having a time and comprising a plurality of intensity values at said time, each of said intensity values having a corresponding distance value representing a distance between said UWB transceiver and said subject;
   determine a Range-Doppler map from said plurality of return signal readings;
   analyze said Range-Doppler map to determine a breathing frequency value of said subject;
   perform null steering of a plurality of Doppler-map frequencies in said Range-Doppler map to nullify said breathing frequency value and integer multiples of said breathing frequency value, to obtain a plurality of combined frequencies comprising a plurality of harmonics of a heartbeat frequency and a plurality of other frequencies, each a sum of an integer multiple of said breathing frequency value and another integer multiple of one of said plurality of harmonics, or a difference between an integer multiple of said breathing frequency value and another multiple of one of said plurality of harmonics; and
   determine a heartbeat frequency value for which a plurality of computed frequencies corresponds with said plurality of combined frequencies, wherein said plurality of computed frequencies comprises a plurality of computed harmonics of said determined heartbeat frequency and a plurality of other computed frequencies, each being a sum of an integer multiple of said breathing frequency value and another integer multiple of one of said plurality of computed harmonics, or a difference between an integer multiple of said breathing frequency value and another multiple of one of said plurality of computed harmonics.

2. The system of claim 1, wherein said transceiver is an impulse radio transceiver.

3. The system of claim 1, wherein said at least one hardware processor is further configured to analyze said Range-Doppler map to determine a breathing frequency value of said subject comprising:

identifying at least one peak frequency in said Range-Doppler map;

performing spectral estimation of each of said at least one peak frequency to obtain at least one sequence of harmonics, each comprising for one of said at least one peak frequency a first harmonic frequency, a second harmonic frequency and a third harmonic frequency of said at least one peak frequency; and determining a breathing frequency value as a difference between frequency values of two consecutive peaks of said at least one sequence of harmonics.

4. The system of claim 3, wherein said performing spectral estimation comprises applying Multiple Signal Classification (MUSIC) or Fast Fourier Transform (FFT) to at least one row of said Range-Doppler map representing a distance having said at least one peak frequency.

5. The system of claim 1, wherein said at least one hardware processor is further configured to perform null steering of said plurality of Doppler frequencies using MUSIC with spectral nulling.

6. The system of claim 1, wherein said at least one hardware processor is further configured to determine said Range-Doppler map from said plurality of return signal readings comprising:

canceling clutter with regard to intensity from each of said plurality of return signal readings, to produce a plurality of intensity-cleaned processed readings;

producing a plurality of bins by partitioning a distance axis of said plurality of return signal readings into an identified amount of bins;

canceling clutter with regard to distance from each of said plurality of intensity-cleaned readings to produce a plurality of distance-cleaned readings;

for each of said plurality of bins, multiplying all intensity values in said plurality of distance-cleaned readings associated with said bin's distances by a window function in time domain to produce a plurality of windowed readings;

applying to said plurality of windowed readings a frequency filter for an identified range of frequencies to eliminate frequencies not relevant to breathing or heartbeat frequencies, to produce a plurality of filtered readings; and applying FFT to each of said plurality of filtered readings to produce a Range-Doppler map.

7. The system of claim 6, wherein said window function is a Hann function window.

8. The system of claim 6, wherein said identified range of frequencies is between 0.1 Hertz and 4 Hertz.

9. The system of claim 1, wherein said at least one hardware processor is further configured to:

send a message to a control hardware processor, subject to a produced breathing frequency value deviating in at least a predetermined threshold from a reference frequency, wherein said reference frequency is selected from the group consisting of: a previously produced breathing frequency and a predetermined reference breathing frequency.

10. The system of claim 9, wherein said predetermined threshold is a relative difference between said produced breathing frequency and said reference frequency.

11. The system of claim 10, wherein said relative difference is 5 percent of said reference frequency.

12. The system of claim 9, wherein said predetermined threshold is an amount of Hertz.

13. The system of claim 1, wherein said at least one hardware processor is further configured to:

send a message to a control hardware processor, subject to a produced heartbeat frequency value deviating in at least a predetermined heartbeat difference threshold from a reference frequency, wherein said reference frequency is selected from the group consisting of: a previously produced heartbeat frequency and a predetermined reference heartbeat frequency.

14. The system of claim 13, wherein said predetermined threshold is a relative difference between said produced heartbeat frequency and said reference frequency.

15. The system of claim 14, wherein said relative difference is 5 percent of said reference frequency.

16. The system of claim 13, wherein said predetermined threshold is an amount of Hertz.

17. The system of claim 6, wherein said at least one hardware processor is further configured to cancel clutter with regard to intensity from each of said plurality of return signal readings by computing an average intensity value of said plurality of intensity values of said reading and subtracting said average intensity value from each of said plurality of intensity values of said reading.

18. The system of claim 6, wherein said at least one hardware processor is further configured to cancel clutter with regard to distance from each of said plurality of intensity-cleaned readings by computing for each distance a second average intensity value of said plurality of intensity values of all of said plurality of intensity-cleaned readings corresponding with said distance, and subtracting said second average intensity value from each of said plurality of intensity values of all of said plurality of intensity-cleaned readings corresponding with said distance.

19. A method for determining heartbeat frequency of a subject, comprising:

receiving a plurality of return signal readings from a UWB transceiver, each of said readings having a time and comprising a plurality of intensity values at said time, each of said intensity values having a corresponding distance value representing a distance between said UWB transceiver and said subject;

determining a Range-Doppler map from said plurality of return signal readings;

analyzing said Range-Doppler map to determine a breathing frequency value of said subject;

performing null steering of a plurality of Doppler-map frequencies in said Range-Doppler map to nullify said breathing frequency value and integer multiples of said breathing frequency value, to obtain a plurality of combined frequencies comprising a plurality of harmonics of a heartbeat frequency and a plurality of other frequencies, each a sum of an integer multiple of said breathing frequency value and another integer multiple of one of said plurality of harmonics, or a difference between an integer multiple of said breathing frequency value and another multiple of one of said plurality of harmonics; and determining a heartbeat frequency value for which a plurality of computed frequencies corresponds with said plurality of combined frequencies, wherein said plurality of computed frequencies comprises a plurality of computed harmonics of said determined heartbeat frequency and a plurality of other computed frequencies, each a sum of an integer multiple of said breathing frequency value and another integer multiple of one of said plurality of computed harmonics, or a difference between an integer multiple of said breathing frequency value and another multiple of one of said plurality of computed harmonics.

* * * * *